United States Patent [19]

Leitert et al.

[11] 4,124,534
[45] Nov. 7, 1978

[54] HIGH TEMPERATURE CHLORINATION CATALYST

[75] Inventors: Frederick C. Leitert, North Madison; Carl G. Vinson, Jr., Mentor, both of Ohio

[73] Assignee: Diamond Shamrock Corporation, Cleveland, Ohio

[21] Appl. No.: 734,249

[22] Filed: Oct. 20, 1976

[51] Int. Cl.$^2$ ............... B01J 27/10; C07C 17/00; C07C 21/02; C07C 21/00
[52] U.S. Cl. ............... 252/441; 260/659 A; 260/656 R; 260/654 A
[58] Field of Search ............... 252/441, 442

[56] References Cited

U.S. PATENT DOCUMENTS

| | | | |
|---|---|---|---|
| 2,636,864 | 4/1953 | Pye et al. | 252/441 |
| 3,148,222 | 9/1964 | Penner et al. | 252/441 X |
| 3,427,359 | 2/1969 | Rectenwald et al. | 252/442 X |
| 3,468,968 | 9/1969 | Baker et al. | 252/442 X |
| 3,624,170 | 11/1971 | Wakiyama et al. | 252/441 X |
| 3,702,311 | 11/1972 | Beard | 252/441 |

Primary Examiner—Patrick P. Garvin
Assistant Examiner—William G. Wright
Attorney, Agent, or Firm—John C. Tiernan

[57] ABSTRACT

The present invention relates to a novel catalyst system for chlorination of hydrocarbons either by oxyhydrochlorination, and/or oxychlorination. The catalyst system comprises copper chloride impregnated onto an alumina support with a metal chloride selected from the group consisting of potassium chloride, lithium chloride, cesium chloride, magnesium chloride, calcium chloride or barium chloride, said alumina support having a sodium oxide content of from 0.2 to about 2.0% by weight and a silica content no more than 4%.

14 Claims, No Drawings

HIGH TEMPERATURE CHLORINATION CATALYST

BACKGROUND OF INVENTION

The use of copper compounds in the halogenation of aliphatic and aromatic hydrocarbons by oxyhydrohalogenation is of course well known in the art. In general, these compounds have been impregnated on a substantially inert support such as silica or alumina or the like. In the patent literature alone, there are literally hundreds of prior art publications discussing the use of cupric chloride per se, catalysts comprising an alumina or silica support impregnated with cupric chloride, and catalyst compositions involving combinations of cupric chloride and other metal chlorides, including potassium and other alkali metal chlorides.

As one example, mention might be made of U.S. Pat. No. 3,148,222 issued Sept. 8, 1964, which discloses and claims a process for chlorinating benzene and other aromatic hydrocarbons using a copper chloride-lithium chloride catalyst of an inorganic catalyst support, the preferred support being activated F-1 alumina which contains about 0.8% sodium oxide.

There are many major process variables which will affect the type and specific properties of the catalyst employed, including such things as the type of reactor (fixed or fluid bed, etc.) the nature of the hydrocarbon feed stock (saturated or unsaturated, aromatic or aliphatic), the source of chlorine or other halogen to be employed (chlorine gas in oxychlorination, hydrochloric acid in oxyhydrochlorination), to mention a few.

In all cases, there are however a number of specific desired chemical, physical or process characteristics which are common to all of the situations. These include in every case, the ability of the catalyst to provide efficient conversion of hydrocarbon feed stock to chlorinated hydrocarbon end products.

In the past, those skilled in the art have sought a socalled "selective catalyst," that is to say a catalyst which would provide selective chlorination of the hydrocarbon feed stock to a very high yield (90% or better) of a single predetermined chlorinated hydrocarbon end product, minimizing the amounts of related chlorinated hydrocarbons produced as by-products. For example in the chlorination of ethylene and/or ethane, to ethylene dichloride, one would expect to also produce at least trace amounts of vinyl chloride, dichloroethylenes, trichloroethylene, trichloroethane, perchloroethane, tetrachloroethane, and pentachloroethane. Thus, in the past, the efficiency of a catalyst was judged by its ability to selectively produce, for example ethylene dichloride, in yields in excess of 90 and preferably in excess of 95%, with corresponding low conversions to other chlorinated hydrocarbons of the ethylene/ethane series, and/or carbon oxides.

SUMMARY OF THE INVENTION

The present invention relates to a novel catalyst system for chlorination of hydrocarbons either by oxyhydrochlorination, and/or oxychlorination. The catalyst system comprises copper chloride modified with at least one metal chloride selected from the group consisting of potassium chloride, lithium chloride, cesium chloride, magnesium chloride, calcium chloride or barium chloride impregnated onto an alumina support, the alumina support having an alumina content of 95% to 99%, a sodium oxide content of from 0.2% to about 2.0% by weight, a silica content less than 4%, an average particle size of from about 50 to 150 microns, and a surface area of from about 1.0 to about 10 m$^2$/gm.

The total loading of catalyst salts should be in the range of from about 3% to about 10%, and the atomic ratio of the modifying metal to copper should be in the range of from about 0.5:1 to about 1.2:1. The resultant catalyst is equally effective for oxychlorination as well as oxyhydrochlorination.

Surprisingly, while the support must contain from about 0.2% to about 2.0% sodium oxide, sodium cannot be substituted for the potassium or lithium, etc. as employed as the catalyst modifier.

The catalyst of the present invention differs from those of the prior art particularly in that it has utility in both oxyhydrochlorination (OHC) and/or oxychlorination (OC) processes. The catalyst also has utility for the direct oxychlorination of ethylene to tri or perchloroethylene. It can also be employed in an OHC process to provide nonselective chlorination of aliphatic hydrocarbon to a mixture of corresponding saturated and unsaturated chlorinated hydrocarbon compounds having a closely controlled predetermined overall average empirical formula. This mixture can be separated by conventional techniques, or the unfractionated mixture can be converted to a more deeply chlorinated hydrocarbon product, e.g., to perchloroethylene by conventional vapor phase chlorination techniques such as those disclosed in U.S. Pat. No. 3,674,881 to Lukes et al.

The novel catalyst system of the present invention also differs from those of the prior art in that it can be employed to achieve, stoichiometric balance or selective imbalance in combined oxyhydrochlorination/vapor phase chlorination process. The novel catalyst thus functions in such a way that it can be employed, for example in the oxyhydrochlorination of ethylene to produce a mixture of chlorinated hydrocarbon products of a specific desired overall empirical formula, for subsequent vapor phase chlorination to perchloroethylene, while selectively being able (a) to employ and utilize any excess hydrochloric acid which may be available, e.g.:

(OHC) C$_2$H$_4$ + 4HCl $\xrightarrow{AIR/O_2}$ C$_2$Cl$_4$ + 4H$_2$O (b) to produce excess hydrochloric acid should this be desirable, e.g.,:

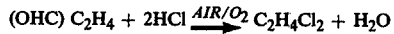
(OHC) C$_2$H$_4$ + 2HCl $\xrightarrow{AIR/O_2}$ C$_2$H$_4$Cl$_2$ + H$_2$O

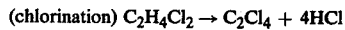
(chlorination) C$_2$H$_4$Cl$_2$ → C$_2$Cl$_4$ + 4HCl

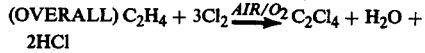
(OVERALL) C$_2$H$_4$ + 3Cl$_2$ $\xrightarrow{AIR/O_2}$ C$_2$Cl$_4$ + H$_2$O + 2HCl (c) to operate as a completely balanced system in which the hydrochloric acid produced by the system, exactly balances that which is required, e.g.,:

(OHC) C$_2$H$_4$ + 3HCl $\xrightarrow{AIR/O_2}$ C$_2$H$_3$Cl$_3$ + 2H$_2$O

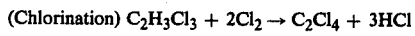
(Chlorination) C$_2$H$_3$Cl$_3$ + 2Cl$_2$ → C$_2$Cl$_4$ + 3HCl

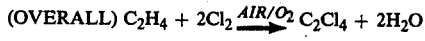
(OVERALL) C$_2$H$_4$ + 2Cl$_2$ $\xrightarrow{AIR/O_2}$ C$_2$Cl$_4$ + 2H$_2$O or (d) to function as an oxychlorination catalyst: (OC)

C$_2$H$_4$ + 2Cl$_2$ $\xrightarrow{AIR/O_2}$ C$_2$Cl$_4$ + 2H$_2$O

Thus, in the process illustrated by the equation (a) above, 4 moles of hydrochloric acid are required for each mole of perchloroethylene produced, thus requiring an available excess hydrochloric acid; while in equation (b) 4 moles of hydrochloric acid are produced in the vapor phase chlorination reaction, only 2 of which can be recycled to the OHC reactor, so that the overall reaction results in the net production of 2 moles of excess hydrochloric acid for each mole of perchloroethylene produced. In equation (c) the 3 moles of hydrochloric acid produced in the vapor phase chlorination process can be recycled to the OHC reactor and will exactly offset the 3 moles of hydrochloric acid needed for the OHC process.

PREFERRED EMBODIMENT

The preferred catalyst of the present invention is copper chloride modified by potassium chloride impregnated on an alumina support, said support having an alumina content of 98% to 99.5%, from about 0.5% to about 1% sodium oxide, a silica content less than 0.5%, an average particle size of from about 90 to about 120 microns, and an average surface area from about 2 to about 5 square meters per gram; the total loading of catalyst salts being from about 5% to about 8% and the atomic ratio of potassium to copper being in the range from about 0.9:1 to 1.2:1.

It is desirable that supports with cul de sac pores be excluded. Such pores would tend to trap the hydrocarbon gases or molecules and promote their oxidation. In both oxychlorination and oxhydrochlorination it is considered desirable that the average por diameter be in the range of 1000 to 5000 Angstroms.

As noted hereinbefore, in the past those skilled in the art have sought selective catalysts, to provide selective oxyhydrochlorination to a very high yield of a single predetermined hydrocarbon end product. For example, one of the more widely employed commercial catalysts for the oxyhydrochlorination of ethylene will yield about a 95% conversion of ethylene to ethylene dichloride with only trace amounts of other chlorinated hydrocarbon. This catalyst, however, can only be employed for production of ethylene dichloride since the higher temperatures (above about 260° C.) and/or higher HCl:ethylene ratios, required to produce a greater depth of chlorination, result in loss of fluidization, and then agglomeration of the bed.

The novel catalyst of the present invention on the other hand maintains good fluidization over extended periods in oxyhydrochlorination at temperatures of from 300° C. to 400° C. and above. For example, in an extended life test of the catalyst of the present invention, the catalyst was employed in the chlorination of ethylene at 340° C. for a period in excess of 72 days without substantial evidence of agglomeration or significant problems in fluidization.

CATALYST PREPARATION

The catalyst was generally prepared by standard procedures well known to those skilled in the art, such as by vacuum impregnation of the support, vacuum filtration of excess impregnating solution, drying, and sieving of the dried catalyst prior to charging to the reactor.

The following example will serve by way of illustration, and not by way of limitation, to describe the experimental procedures which were employed in the preparation of the catalyst, and in conducting the laboratory oxyhydrochlorination reaction in which it was evaluated.

In preparing a standard 300 cc charge of catalyst for the reactor, 400 grams of the desired support was placed in a flask connected to a separatory or addition funnel, and aspirated for twenty minutes before addition of the impregnating solution. The impregnating solution was prepared by dissolving the requisite amounts of copper chloride and potassium chloride in deionized water. The solution was run onto the support in a thin stream and the flask was tilted and rolled to distribute the stream evenly over the support. In order to facilitate subsequent handling, the volume of impregnating solution added to the aspirated support was approximately twice the volume to be imbibed into the pores of the support. The slurry was shaken under full aspiration for approximately two minutes, with the total contact between the support and the impregnating solution being limited to four minutes overall (from the start of impregnation) in order to limit any potential preferential adsorption by the support of one of the individual catalyst salts. On release of the vacuum, the slurry was vigorously shaken for about one minute, and filtered through a Buchner funnel. Aspiration of the filter cake was continued for from about 40 to about 60 minutes to clear the interstices of the wet cake of as much excess impregnating solution as possible, so as to minimize the coating of catalyst salts on the exterior of the particles. The filtered cake was transferred to a ceramic dish, and dried at 150° C. for 8 hours, after which the dried solids were sieved through a 60 mesh screen, with oversized particles being discarded.

OHC EVALUATION

Evaluation of the catalyst in a fluid bed OHC reactor system was carried out in a vertical reactor having a 1.5-inch ID cylindrical Pyrex reaction zone. Either an 18-inch or a 24-inch cylinder was employed depending upon the designated contact time. Cylinder ethylene, HCl, and air (metered at 10 psig with calibrated rotameters) were mixed in a pipe tee, and fed without preheating to the bottom of the reactor through a 30 ml. Pyrex frit filter (which served as the distributor plate) to which the bottom of the reactor had been sealed.

The top of the reactor, at a point above the top of the catalyst bed was sealed to a bulbous upper section having an access port at its top which served as a charging port for addition of the catalyst. The access port had a standard taper joint to accommodate a one-hole rubber stopper through which a 5 mm. ID Pyrex thermowell was inserted during operation of the reactor, so that the thermowell was positioned vertically along the axis of the reactor, and extended to within one inch of the frit. The reactor surfaces from the frit to the top of the upper section were heated via a helical winding of 20-gauge Nichrome wire, the turns being spaced at about ⅜ inch over the cylindrical section and at about 1 inch over the enlarged surface of the upper section. The windings on the vertical surfaces were covered with Fiberglas pipe insulation, with bed fluidization and particle motion being observed through long vertical holes in the insulation. Reactor effluent gasses were taken off through a separate egress port in the upper section through a 9 ml. ID tube. The reaction effluent gasses passed from the 9 mm. tube through a isopropyl alcohol cooled (0° C.) helical condenser to a collection flask immersed in an isopropyl alcohol dry ice mixture, the top of the collecting flask being connected to a thimble condenser having a 3 × 12-inch cavity which was also packed with an isopropyl alcohol dry ice mixture.

OPERATING PROCEDURE

Where a 10-second contact time was desired, the 18-inch cylindrical section was employed and was charged with 300 cc (loosely packed) of the catalyst to be tested. Where a 15 second contact time was desired, the 24-inch cylindrical reaction zone was employed, and was charged with 450 cc of catalyst. Once charged, the reactor was positioned with the cylindrical section in a vertical position, and air was passed through the catalyst bed at about one liter per minute through the heated reactor to drive off any last traces of moisture. When the bed had expanded, the thermowell was aligned and secured, with the thermocouple normally located at about an inch above the bottom of the thermowell. Fluidization was normally observed after the catalyst had reached a temperature of about 300°C., (the air flow being increased and/or the thermowell being used to stir the bed, if any stagnant zones were observed). Once the catalyst was moving freely, the feed gases were set at the predetermined rates, the temperatures brought to the desired level, and the reactor was run, if possible, for 16 hours at a given set of conditions, before collecting condensate for analysis or analyzing of samples of the uncondensed gas. Analysis of organic liquid and gaseous effluents were performed by gas chromatography.

TEST CATALYST

Unless either otherwise indicated or clear from the context, the terms "catalyst of the present invention" refers to a catalyst prepared by impregnating Alcoa A-3 alumina with 3.9 weight percent copper chloride and 2.4 weight percent potassium chloride, a total loading of catalyst salts of about 6.3%, and a K:Cu atomic ratio of 1.1:1. It should be clearly understood, however, that this is merely one of a wide number of specific catalysts which would fall within the preferred ranges of the present invention and that it merely happens to be the specific catalyst arbitrarily selected for evaluation in early testing, and thereafter employed to provide a valid basis for comparative evaluation.

It should also be clearly understood that the total loading of catalyst salts and the ratio of potassium to copper discussed herein, refer to the catalyst in use. In other words, these would be the loading of catalyst salts and atomic ratios for the freshly-prepared catalyst employed in the original charge to the reactor.

In commercial OHC reactors, elutriation losses of 10% or more per year are not uncommon, and "make-up catalyst" is added from time to time to replace these losses. It is also to be anticipated, that the use of the catalyst of the present invention in a commercial reactor over a prolonged period would also result in a gradual evaporation loss of cupric chloride. The evaporation loss would be expected to vary according to reaction conditions, particularly temperature.

For example, it has been calculated that while only about 0.5% of the cupric chloride would evaporate in a year's use at temperatures of approximately 340°–350° C., at temperatures of 420° C., losses of 3–6% or more could be encountered. For this reason, the catalyst loading and particularly the ratio of potassium chloride to copper chloride in the make-up catalyst may have to be adjusted to a significantly higher copper chloride level, so that when the make-up catalyst is added to the reactor, and admixed with the catalyst already present, the overall atomic ratio of potassium to copper in the bed will be adjusted to approximately that of the fresh catalyst salts originally charged to the reactor.

While it is possible to closely approximate the copper chloride evaporation losses by calculation based on reaction conditions, it is clearly preferable to adjust the potassium to copper ratio in the make-up catalyst by actual quantitive data. This data can be acquired directly from analysis of periodic samplings of the catalyst bed, or indirectly, from any of a number of sources, such as monitoring of the copper content of the aqueous condensate from the reactors.

Table I contrasts the reaction products produced by the commercial OHC catalyst referred to hereinbefore (at 230° C.) with those produced by the catalyst of the present invention (in a pilot plant reactor) at reactor temperatures of 310° C., 340° C. respectively. The commercial catalyst comprises a alumina having a surface area of 180 m$^2$/gm, a Na$_2$O content of 0.02% and a 14% loading of copper chloride. The pilot plant experiments employed a 6-inch diameter nickel reactor. These pilot scale experiments yielded results consistent with, and equivalent to, those observed in the bench scale experiments. The pilot scale reactor also permitted investigation of increased pressures and superficial gas velocity.

The results for the commercial catalyst are based on actual commercial experience. For this reason, there was no specific separate analysis of the amounts of each of the other individual chlorinated ethylene products present, however, all of these products taken cumulatively represent little more than trace amounts. Attempts to employ the commercial catalyst at temperatures in excess of 260° C., or to employ feeds having an HCl to ethylene ratio in excess of 2:1, caused loss of fluidization and agglomeration of the bed.

In examining Table I, it will be noted that in accordance with accepted practice, the feed ratio of ethylene:hydrogen chloride: air is varied according to the depth of chlorination anticipated. In tables hereinafter, catalyst salts are adjusted to provide higher loadings for supports having a higher surface area. Such changes represent accepted techniques well known to those skilled in the art, for adjusting known variables to maintain optimum reaction conditions.

In the case of the commercial catalyst, ethylene:HCl ratios in excess of 1:2 result in loss of fluidization and agglomeration of the bed. In the case of the catalyst of the present invention, the feed ratio represents the approximate optimum feed ratio based on the previously-observed depth of chlorination obtained at the given temperatures. A higher ratio of hydrogen chloride to ethylene did not result in any significant change in the depth of chlorination obtained.

The inability of the commercial catalyst to provide a depth of chlorination greater than ethylene dichloride creates significant economic as well as environmental problems. Where the ultimate desired end product is tri or perchloroethylene, a catalyst which can provide oxyhydrochlorination only to ethylene dichloride will result in an overall stoichiometric imbalance of the type described by the equations in alternative (b) noted hereinbefore, in which the subsequent vapor phase chlorination reaction produces four moles of hydrochloric acid, only two of which can be recycled to the oxyhydrochlorination reactor. This creates a "captive" producer of significant quantities of hydrochloric acid, often in excess of all internal and external demand. The excess HCl is not only economically undesirable, it is also environmentally undesirable and impossible to simply off-vent.

Tables II and III illustrate the flexibility of the catalyst of the present invention both as to empirical formula of the product produced and the variety of feedstocks which can be employed.

TABLE 1

|  | Commercial Catalyst* | Catalyst of Present Invention | | |
|---|---|---|---|---|
| Reactor Temperature (° C) | 230 | 310 | 340 | 380 |
| Operating Pressure (PSIG) | 45 | 45 | 45 | 45 |
| Molar Feed Ratio ($C_2H_4$; $HC_L$:AIR) | 1:2:4 | 1:2.2:4 | 1:3:6 | 1:3.5:8 |
| Contact Time (SEC) | 25 | 20 | 20 | 20 |
| Superficial Velocity (FT/SEC) | 1.6 | .4 | .4 | .4 |
| Reaction Products (Mole %) | | | | |
| VCM ($C_2H_3CL$) | | 0.5 | 1.1 | 12 |
| DCE's ($C_2H_2Cl_2$) | | | 0.7 | 4.5 |
| EDC ($C_2H_4Cl_2$) | 95 | 86.5 | 50.3 | 8 |
| TCE ($C_2H\ Cl_3$) | | | 1.1 | 1.1 |
| TCA ($C_2H_3Cl_3$) | | 10.0 | 23 | 12 |
| PCE | | — | 2.6 | 24.4 |
| TET ($C_2H_2Cl_4$) | | 1.5 | 13.5 | 11 |
| PENTA ($C_2HCl_5$) | | 0.2 | 4.5 | 11 |
| Percent Saturation (%) | | 99 | 94 | 45 |
| Average Formula | (1) | (2) | (3) | (4) |
| Ethylene Conversion (%) | 95 | 90 | 98 | 100 |
| Ethylene Selectivity (%) | | | | |
| Chlorohydrocarbons | 95 | 98.7 | 96 | 94.5 |
| Carbon Oxides | 5 | 1.3 | 4 | 5.5 |

*Commercial Catalyst - 14% by weight $CuCl_2$ on alumina with 0.02% $Na_2O$ and a surface area of 180 $m^2$/gm.
(1) $C_2H_4Cl_2$
(2) $C_2H_{3.9}Cl_{2.1}$
(3) $C_2H_{3.2}Cl_{2.7}$
(4) $C_2H_{1.6}Cl_{3.3}$

TABLE II

Effect of Temperature on Reaction Product Mix

| Temp ° C | Molar Feed Ratio $C_2H_4$: HCl:Air | $C_2H_4$ Conv. | % Carbon Selectivity to Products** | | | | | | | | | | % Organic Unsat. | Empirical Formula or Organic on $C_2$ Basis*** |
|---|---|---|---|---|---|---|---|---|---|---|---|---|---|---|
| | | | CO+ CO2 | VCM | DEC | EDC | CCl4 | TCE | TCA | PCE | Tetra | Penta | Hexa | | |
| 300 | 1:2.5:5 | 90 | 2 | — | — | 97 | — | — | 1 | — | — | — | — | 0 | $C_2H_{3.99}Cl_{2.01}$ |
| 310 | 1:2.5:5 | 90 | 2 | — | — | 88 | — | — | 10 | — | — | — | — | 0 | $C_2H_{3.9}Cl_{2.1}$ |
| 320 | 1:2.5:5 | 100 | 2 | 1.5 | 0.5 | 73.7 | 0.5 | — | 19 | — | 2.4 | 0.4 | — | 2 | $C_2H_{3.7}Cl_{2.26}$ |
| 330 | 1:3:6 | 100 | 2 | 23 | 3.3 | 34 | 0.7 | 0.5 | 27 | 0.5 | 7 | 2 | 0 | 27 | $C_2H_{3.16}Cl_{2.3}$ |
| 340 | 1:3:6 | 100 | 4 | 28 | .7 | 17 | 0.7 | 2.5 | 25 | 1 | 11 | 3.8 | — | 40 | $C_2H_{2.8}Cl_{2.4}$ |
| 350 | 1:3.5:7 | 100 | 4 | 30 | 16 | 2 | 0.7 | 11 | 13.6 | 3.3 | 12.4 | 7 | — | 62 | $C_2H_{2.32}Cl_{2.53}$ |
| 360 | 1:3.5:7 | 100 | 5.5 | 18 | 22 | 0.6 | 0.8 | 6 | 8 | 7 | 12 | 10 | 0.1 | 66 | $C_2H_{1.85}Cl_{2.83}$ |
| 380 | 1:4:8 | 100 | 4.5 | 8 | 14 | — | 0.6 | 30 | 3.7 | 17 | 10 | 12 | 0.2 | 72 | $C_2H_{1.31}Cl_{3.25}$ |
| 400 | 1:4:9 | 100 | 5 | 2.5 | 6 | — | 0.8 | 34 | 0.4 | 41 | 2 | 8 | 0.3 | 86 | $C_2H_{0.73}Cl_{3.55}$ |

10 Sec. Contact time based on settled bed and feed gas flow at conditions.
Superficial feed gas velocity is 0.1 ft./sec.
**By on-line VPC.
***$CCl_4$ is converted to $C_2$ equivalent by treating as $C_2H_{-1}Cl_7$.

TABLE III

FEEDSTOCK FLEXIBILITY
OHC AND OC TO PCE AND TCE

|  | 1 | 2 | 3 | 4 | 5 |
|---|---|---|---|---|---|
| FEED RATIO | | | | | |
| $C_2H_4$:HCl:AIR | 1:4:9 | | | | |
| $C_2H_4$:$CL_2$:AIR | | 1:2:5 | | | |
| EDC:$CL_2$:AIR | | | 1:1:5 | | |
| EDC:$CL_2$:$O_2$ | | | | 1:1:1 | |
| VHE*:$CL_2$:AIR | | | | | 1:0.75:4.5 |
| REACTION PRODUCTS (%) | | | | | |
| VCM, DEC's, EDC | 9.5 | 6 | 4 | 6 | 6 |
| $CCl_4$ | 0.2 | 1 | 2 | 1 | 1 |
| TCE | 19 | 17 | 17 | 19 | 17 |
| PCE | 58 | 58 | 60 | 56 | 53 |
| TCA, TETRA's, PENTA | 6.5 | 8.5 | 7.5 | 13.5 | 13.5 |
| HEXA | 0.2 | 1 | 1 | 0 | 0 |
| HCB, HCBD | 0.1 | 0.5 | 0.5 | 0.5 | 0.5 |
| ETHYLENE YIELD (%) | | | | | |
| CHLOROHYDRO-CARBONS | 93.5 | 92 | 92 | 96 | 91 |
| CARBON OXIDES | 6.5 | 8 | 8 | 5 | 8 |

All at 420° C, 10 Sec. Contact Time
*unfractionated heavy ends from a commercial vinyl chloride reactor From an examination of Table II, it will be clear that as the temperature is increased from 300° C. to 400° C., the depth of chlorination and the degree of unsaturation are progressively increased. At 300° C., the catalyst actually functions as a highly selective catalyst to the production of EDC: at 350° C., the overall empirical formula approximates trichloroethane; and at 400° C. the product is highly chlorinated and highly unsaturated with a 75% yield of a mixture of tri- and perchloroethylene.

Table III also presents pilot plant data. From Table III it will be seen that the novel catalyst of the present invention can be employed for either oxyhydrochlorination or oxychlorination of saturated or unsaturated feedstocks, or even mixed feedstocks such as the mixed chloro-hydrocarbon by-products which form the heavy ends in the commercial VCM reactor. Table III also illustrates that the catalyst can be employed to produce a high percentage of trichloroethylene and perchloroethylene without the necessity for subsequent vapor phase chlorination. In this regard, the results obtained with the VHE feedstock are quite significant, since they indicate that on separation of the trichloro- and perchloro-, the remaining chlorohydrocarbons could be continuously recycled to the reactor.

In summary, Tables II and III clearly demonstrate that the catalyst of the present invention can be employed:

1. For selective oxyhydroclorination of ethylene to ethylene dichloride in yields equal or better than those provided by presently employed commercial OHC catalysts;

2. For non-selective oxyhydrochlorination of olefins, or partly chlorinated olefins, to a mixture of chlorinated olefins having a controllable overall empirical formula, for subsequent vapor phase chlorination to highly unsaturated, deeply chlorinated chlorohydrocarbons;

3. Oxhydrochlorination or oxychlorination of a wide variety of feedstocks to a high yield of highly unsaturated, highly chlorinated chlorohydrocarbons, including a continuous process in which the desired end products are removed and any chlorohydrocarbon by-products are continuously recycled through the reactor as feedback.

It has been noted hereinbefore that the catalyst of the present invention is on an alumina support having an alumina content of 95% to 99%; a sodium oxide content of 0.2% to about 2.0% by weight; and a silica content less than 4%; and a surface area of from about 1.0 to about 10 $m^2/gm$. Table IV describes several supports which are suitable for catalyst of the present invention. The criticality of the support is illustrated in Table V wherein a wide variety of alumina and silica alumina supports are compared.

An examination of Table V discloses that supports 7, 9 and 10 yield acceptable results, and each fall within the limits described hereinbefore. The other supports fail to provide satisfactory results, and each fails to meet at least one of the defined limitations. The first six supports all have a sodium oxide content below 0.2%, while support No. 11 has too high a sodium oxide content. Support No. 8 has a surface area below the minimum in the range defined hereinbefore.

Support No. 10 is a relatively impure alumina with 3% silica and 0.8% $Na_2O$. While it can be employed for non-selective oxyhydrochlorination to produce chlorinated hydrocarbon products having the empirical formula approximating Trichloroethylene, the use of supports with significantly greater silica content, is likely to result in agglomeration and/or high selectivities to carbon oxides.

TABLE IV

Properties of Suitable Alumina Supports

|  | Alcoa Aluminas* | | Carborundum Aluminas** | | |
|---|---|---|---|---|---|
|  | A-1 | A-3 | SAEHS-33 | SAEHS-3 | SAEHS-1 |
| Chemical Analysis, % | | | | | |
| $Al_2O_3$ | 99 | 99 | 99 | 99 | 96 |
| $Na_2O$ | 0.5 | 0.5 | 0.5 | 0.5 | 0.8 |
| $Fe_2O_3$ | 0.04 | 0.04 | 0.04 | 0.1 | 0.02 |
| $SiO_2$ | 0.025 | 0.025 | 0.05 | 1.3 | 3.3 |
| Loss on ignition at 1100° C | 0.75 | 0.50 | | | |
| Alpha alumina content | | 80 | | | |
| Physical Properties | | | | | |
| Surface area, $M^2/g$ | ~10 | 5 | 4 | 2.3 | 1.9 |
| Pore volume, cc/g | 0.25 | ~0.25 | 0.32 | 0.23 | 0.25 |
| Average pore diameter, A | ~1,000 | 2,000 | 3,200 | 4,000 | 5,200 |
| Packed bulk density, g/cc | 1.1 | 1.1 | 1.2 | 1.2 | 1.2 |
| Average particle diameter, μ | ~90 | ~90 | 120–150 | 90–120 | 90–120 |

TABLE V

Comparison of Catalyst Supports

| Support Composition | $Na_2O$ Content (%) | Surface Area ($m^2/gm$) | Composition (wt%) | Temperature Range (° C) | Maximum HCl/$C_2H_4$ Ratio | Depth of Chlorination | Comments |
|---|---|---|---|---|---|---|---|
| 1) Harshaw -alumina | 0.02 | 180 | $CuCl_2$-14 | 220–290 | 2.5 | $C_2H_4Cl_2$— | agglomerated above 290° C |
|  | 0.02 | 100 | $CuCl_2$-10 KCl-2 | 290 | 2 | $C_2H_{3.5}Cl_{2.5}$ | also low ethylene conversion; agglomerated above 290° C |
| 2) Grace silica | — | 285–600 | $CuCl_2$-11 KCl-6 | agglomerates >250° C | agglomerated in presence of HCl | — | all silicas agglomerated in the presence of HCl |
| Grace silica-aluminas | | | | | | | |
| 3) 13% alumina | 0.02 | ~400 | $CuCl_2$-11 KCl-6 | " | " | — | same problem encountered with silica supports |
| 4) 28% alumina | 0.04 | ~400 | $CuCl_2$-11 KCl-6 | " | " | — |  |
| -alumina | | | | | | | |
| 5) Harshaw | 0.02 | 5 | $CuCl_2$-5.6 KCl-2.3 | ~300 | ~2.0 | $C_2H_4Cl_2$ | poor fluidization above 300° C |
| 6) Harshaw | 0.02 | 30 | $CuCl_2$-13 KCl-5.6 | 300–230 | 2.5 | $C_2H_{3.6}Cl_{2.4}$ | poor fluidization above 325° C |
| 7) Alcoa A-1 | 0.5 | 10 | $CuCl_2$-4 KCl-1.6 | 300–360+ | 4.5 | $C_2H_4Cl_2$— $C_2H_{2.4}Cl_{3.6}$ | temperatures above 360° C not yet explored |
| 8) Alcoa A-2 | 0.5 | 0.4 | $CuCl_2$-4.1 KCl-1.7 | 300–320 | 3 | $C_2H_{3.9}Cl_{2.1}$ | only 90% ethylene conversion at 320° C |
| 9) Alcoa A-3 | 0.5 | 5 | $CuCl_2$-4 KCl-2.4 | 300–420+ | 4.5 | $C_2H_4Cl_2$— $C_2H_{1.2}Cl_{4.8}$ | have not explored temperatures above 420° C |
| 10) Carborundum alumina 3% silica | 0.8 | 1.9 | $CuCl_2$-2.2 KCl-0.9 | 300–350 | 3 | $C_2H_4Cl_2$— $C_2H_{2.8}C_{3.2}$ | onset of poor fluidization at 350° C |
| 11) Alcoa D-10031 | 7 | 1.2 | $CuCl_2$-1.6 KCl-0.3 | 300–350 | not established | | agglomeration of particles at 300° C, the only conditions examined |

TABLE VI

Effect of Catalyst Composition on Activity of Catalysts

| Catalyst** | Temp. ° C | Molar Feed Ratio | Sel. to CO + $CO_2$ | Empirical Formula of Organic Condensate | Liq. Comp., Mole % | | | Notes |
|---|---|---|---|---|---|---|---|---|
|  |  |  |  |  | Vinyl | DCE | Total Unsat. |  |
| 3.9% $CuCl_2$ and | 330 | 1:3:6 | 4 | $C_2H_{3.42}Cl_{2.38}$ | 1.7 | 7.5 | 10 |  |
| 1.3% KCl | 340 | 1:3:6 | 5.1 | $C_2H_{2.78}Cl_{2.58}$ | 11.6 | 16.7 | 32 | Bed stagnant |
| K:Cu=0.6:1 | 350 | 1:4:8 | 6 | $C_2H_{2.01}Cl_{2.52}$ | 9.5 | 54.0 | 74 | at bottom. |
| 3.9% $CuCl_2$ | 340 | 1:3:6 | 4 | $C_2H_{2.85}Cl_{2.55}$ | 13.1 | 14.4 | 35 |  |

TABLE VI-continued
Effect of Catalyst Composition on Activity of Catalysts

| Catalyst** | Temp. °C | Molar Feed Ratio | Sel. to CO + $CO_2$ | Empirical Formula of Organic Condensate | Liq. Comp., Mole % | | | Notes |
|---|---|---|---|---|---|---|---|---|
| | | | | | Vinyl | DCE | Total Unsat. | |
| 1.6% KCl, | 350 | 1:4:8 | 6.5 | $C_2H_{1.73}Cl_{2.56}$ | 10.0 | 58.2 | 85 | |
| 3.7% $CuCl_2$ and | 340 | 1:3:6 | 4 | $C_2H_{2.41}Cl_{2.14}$ | 25.8 | 41.6 | 72 | |
| 2.1% KCl; | 350 | 1:4:8 | 7.2 | $C_2H_{2.05}Cl_{2.3}$ | 16.2 | 55 | 82 | |
| K:Cu=1:1 | 360 | 1:4:8 | 4 | $C_2H_{2.05}Cl_{2.57}$ | 9.1 | 48.0 | 69 | |
| 3.9% $CuCl_2$ and | 340 | 1:3:6 | 3.8 | $C_2H_{2.54}Cl_{2.32}$ | 15.7 | 38.6 | 57 | |
| 2.4% KCl; | 350 | 1:4:8 | 9.4 | $C_2H_{1.98}Cl_{2.18}$ | 12.5 | 69.3 | 92 | |
| K:Cu-1.1:1 | 360 | 1:4:8 | 5.6 | $C_2H_{1.98}Cl_{2.69}$ | 7.5 | 48.7 | 67 | |
| | 370 | 1:4:8 | 5 | $C_2H_{1.73}Cl_{2.99}$ | 2.9 | 38.0 | 64 | |
| | 380 | 1:4:9 | 5.4 | $C_2H_{1.23}Cl_{3.44}$ | 1.2 | 20.4 | 67 | |
| | 390 | 1:4:9 | 6.4 | $C_2H_{1.2}Cl_{3.29}$ | 1.2 | 26.3 | 75 | |
| | 400 | 1:4:9 | 6.3 | $C_2H_{0.9}Cl_{3.49}$ | 0.7 | 16.8 | 71 | |
| 3.8% $CuCl_2$ and | 340 | 1:3:6 | 4.5 | $C_2H_{3.25}Cl_{2.65}$ | 0.1 | 5 | 5 | |
| 2.5% KCl; | 350 | 1:4:8 | 5 | $C_2H_{2.62}Cl_{3.0}$ | 7.4 | 5.7 | 18 | |
| K:Cu=1.2:1 | 360 | 1:4:8 | 5 | $C_2H_{2.2}Cl_{3.2}$ | 8.2 | 5.6 | 30 | |
| | 380 | 1:4:8 | 5 | $C_2H_{1.7}Cl_{3.3}$ | 7.6 | 8.1 | 50 | |
| | 400 | 1:4:9 | 6 | $C_2H_{1.2}Cl_{3.54}$ | 2.0 | 6.3 | 63 | |

*10-Second contact throughout based on settled bed and feed gas flow at conditions Alcoa A-3 support.
**Calculated composition. K:Cu ratios are calculated atomic ratios.

Table VI illustrates the effective catalyst composition on activity of the catalyst. It will be noted that an atomic ratio of potassium to copper of 0.6:1 is suitable for use in non-selective OHC only to temperatures of about 350° C., where it can be employed for non-selective oxyhydrochlorination to give a product having an empirical formula of approximately trichloroethane. As the atomic ratio is increased from 0.6:1 to 1.1:1, increasingly higher temperatures and greater depth of chlorination can be obtained without undue increase in $CuCl_2$ evaporation. At an atomic ratio of 1.2:1, however, the depth of chlorination and the yield of highly-chlorinated unsaturated product begins to decline.

In order to maintain a valid basis for comparison of the various test results, the foregoing discussion has been primarily directed at the chlorination of ethylene using a potassium chloride-copper chloride catalyst in a fluid bed reactor. It should again be noted, however, that the foregoing Tables and experiments are presented by way of illustration and not by way of limitation. The catalyst of the present invention is not limited to the chlorination of ethylene in a fluid bed but has utility in fixed or fluid bed oxyhalogenation and/or oxyhydrohalogenation of a wide variety of olefin hydrocarbons, and particularly $C_2$ to $C_5$ alpha olefins and their chlorine-containing derivatives.

Likewise other alkali metal chlorides and alkaline earth metal chlorides, with the single exception of sodium chloride, can be substitued for the potassium chloride. While catalysts composed of copper chloride and one of these other modifying metal chlorides will provide results substantially similar to those obtained with potassium chloride, as described hereinbefore, potassium chloride is the preferred modifying metal chloride, and appears to provide optimum results.

Again, while there is a critical level of sodium oxide which must be present in the support, sodium chloride is the only alkali metal chloride or alkaline earth metal chloride which has been found to be unsuitable for use as the modifying metal chloride in preparing the catalyst of the present invention. While I am unwilling to subscribe to any single theory which might explain the foregoing, it would appear that the unsuitability of sodium chloride as a modifying metal chloride may be a function of its crystal structure which is substantially different from that of the other alkali chlorides which were found to be suitable.

It will, of course, be obvious that still other changes and variations, specific materials, procedures, apparatus and the like can be made without departing form the scope of the invention herein disclosed, and it is my intention to be limited only by the appended claims.

The embodiments of the invention in which an exclusive property or privilege is claimed are defined as follows:

1. A catalyst for halogenation of olefinic hydrocarbons consisting essentially of cupric chloride modified with at least one modifying metal chloride selected from the group consisting of potassium chloride, magnesium chloride, calcium chloride and barium chloride; impregnated onto an alumina support, said alumina support having an alumina content of from about 96% to about 99% by weight; a silica content of from 0 to about 4.0% by weight; a sodium oxide content of from about 0.2% to about 2.0% by weight, an average particle size of from about 50 to 150 microns, and a surface area of from about 1.0 to about 10 $m^2/gm$; the total loading of catalyst salts being in the range of from about 3% to about 10% by weight and the atomic ratio of said modifying metal to copper being in the range of from about 0.5:1 to about 1.2:1.

2. The catalyst according to claim 1 wherein said modifying metal chloride is potassium chloride.

3. The catalyst according to claim 1 wherein said support is an $\alpha$ alumina support.

4. The catalyst according to claim 1 wherein said support is an alumina silica support having a silica content of from about 0.4 to about 4.0 percent by weight, based on the weight of the support.

5. The catalyst according to claim 1 wherein said catalyst is an admixture of used catalyst which has already been employed in a halogenation process and make-up catalyst; said used catalyst having an atomic ratio of modifying metal to copper of less than 0.5:1, and said admixture having an atomic ratio modifying metal to copper in the range of from 0.5:1 to about 1.2:1.

6. The catalyst according to claim 1 wherein said alumina support has an alumina content of 98% to 99.5%; a sodium oxide content of from about 0.5% to about 1.0%; an average particle size of from about 90 to about 120 microns; an average surface area from about 2 to about 5 square meters per gram; the total loading of catalyst salts is from about 5% to about 8%; ad the atomic ratio of modifying metal to copper being in the range from about 0.9:1 to 1.2:1.

7. The catalyst according to claim 6 wherein said modifying metal chloride is potassium chloride.

8. The catalyst according to claim 7 wherein said support is an α alumina support.

9. The catalyst according to claim 6 wherein said catalyst is an admixture of used catalyst which has already been employed in a halogenation process and make-up catalyst; said catalyst having an atomic ratio of modifying metal to copper in excess of 1.2:1, said make-up catalyst having an atomic ratio of modifying metal to copper of less than 0.9:1, and said admixture having an atomic ratio modifying metal to copper in the range of from 0.9:1 to about 1.2:1.

10. The catalyst according to claim 6 wherein said alumina support is substantially free of cul-de-sac pores and has an average pore diameter between 1000–5000 Angstroms.

11. A catalyst for chlorination of $C_2$ hydrocarbons consisting essentially of cupric chloride modified with a modifying metal chloride selected from the group consisting of potassium chloride, calcium chloride and barium chloride; impregnated onto an alumina support, said alumina support having an alumina content of from about 98% to about 99.5% by weight; a silica content of from 0 to about 2.0% by weight; a sodium oxide content of from about 0.5% to about 1.0% by weight, an average particle size of from about 90 to 120 microns, and a surface area of from about 2.0 to about 5 $m^2/gm$; the total loading of catalyst salts being in the range of from about 5% to about 8% by weight and the atomic ratio of said modifying metal to copper being in the range of from about 0.5:1 to about 1.2:1.

12. The catalyst according to claim 11 wherein said modifying metal chloride is potassium chloride.

13. The catalyst according to claim 11 wherein said support is an alpha alumina support.

14. The catalyst according to claim 11 wherein said catalyst is an admixture of used catalyst which has already been employed in fluid bed halogenation, and make-up catalyst; said used catalyst having an atomic ratio of modifying metal to copper in excess of 1.2:1, said make-up catalyst having an atomic ratio of modifying metal to copper of less than 0.5:1, and said admixture having an atomic ratio modifying metal to copper in the range of from 0.5:1 to about 1.2:1.

* * * * *